United States Patent
Ueno et al.

(10) Patent No.: US 11,660,262 B2
(45) Date of Patent: May 30, 2023

(54) COSMETIC BASE AND SKIN COSMETIC USING SAME

(71) Applicant: SHISEIDO COMPANY, LTD., Tokyo (JP)

(72) Inventors: Kento Ueno, Yokohama (JP); Ayako Ibe, Yokohama (JP); Masayuki Kikuta, Yokohama (JP); Ayaka Hori, Yokohama (JP); Daiki Fujimaki, Yokohama (JP)

(73) Assignee: SHISEIDO COMPANY, LTD., Toyko (JP)

(*) Notice: Subject to any disclaimer, the term of this patent is extended or adjusted under 35 U.S.C. 154(b) by 0 days.

(21) Appl. No.: 16/642,204

(22) PCT Filed: Aug. 29, 2018

(86) PCT No.: PCT/JP2018/031890
§ 371 (c)(1),
(2) Date: Feb. 26, 2020

(87) PCT Pub. No.: WO2019/044880
PCT Pub. Date: Mar. 7, 2019

(65) Prior Publication Data
US 2020/0352845 A1    Nov. 12, 2020

(30) Foreign Application Priority Data

Aug. 31, 2017 (WO) .................. PCT/JP2017/031338

(51) Int. Cl.
A61K 8/73 (2006.01)
A61K 8/04 (2006.01)
A61K 8/81 (2006.01)
A61K 8/86 (2006.01)
A61Q 19/00 (2006.01)
A61K 8/87 (2006.01)
A61K 8/91 (2006.01)
A61K 8/92 (2006.01)

(52) U.S. Cl.
CPC ............. *A61K 8/732* (2013.01); *A61K 8/042* (2013.01); *A61K 8/731* (2013.01); *A61K 8/8152* (2013.01); *A61K 8/86* (2013.01); *A61K 8/87* (2013.01); *A61K 8/91* (2013.01); *A61K 8/92* (2013.01); *A61Q 19/00* (2013.01); *A61K 2800/48* (2013.01)

(58) Field of Classification Search
CPC ........ A61K 8/732; A61K 8/042; A61K 8/731; A61K 8/8152; A61K 8/86; A61K 8/87; A61K 8/91; A61K 8/92; A61K 2800/48; A61Q 19/00
See application file for complete search history.

(56) References Cited

U.S. PATENT DOCUMENTS

2014/0288191 A1    9/2014    Kim

FOREIGN PATENT DOCUMENTS

| JP | 2000-239120 | 9/2000 | |
| JP | 2002-265780 | 9/2002 | |
| JP | 2011-256154 | 12/2011 | |
| JP | 2014-040385 | 3/2014 | |
| JP | 2015-030698 | 2/2015 | |
| JP | 2015-034132 | 2/2015 | |
| JP | 2015030698 A | 2/2015 | |
| JP | 2015-166418 | 9/2015 | |
| JP | 2015-224212 | 12/2015 | |
| JP | 2016-510726 | 4/2016 | |
| WO | WO-2011136270 A1 * | 11/2011 | ............. A61K 47/34 |
| WO | WO 2014/132783 | 9/2014 | |

OTHER PUBLICATIONS

PCT/JP2018/031890 International Search Report (ISR) and Written Opinion (WO), dated Sep. 25, 2018 5 pages—English, 7 pages—Japanese.
Database GNPD [Online]; MINTEL;Dec. 9, 2014 (Dec. 9, 2014), Brand: Avon Anew Men; anonymous: "2-in-1 Gel Cleanser", XP055797408,Database accession No. 2833223; the whole document *, www.gupd.com;3 pages—English.
EP 18850751.1, Extended European Search Report dated May 4, 2021, 7 pages—English.
EP 18850751.1, Supplementary European Search Report dated May 21, 2021, 1 page—English.

* cited by examiner

*Primary Examiner* — Snigdha Maewall
(74) *Attorney, Agent, or Firm* — Andrew F. Young; Nolte Lackenbach Siegel

(57) ABSTRACT

The invention provides a cosmetic base having an unprecedented appearance and feeling on use, in particular a cosmetic base with a novel feeling on use that gives a fresh feeling and a unique feel as the cosmetic softly bursts and collapses, allowing water to flow out, when applied to the skin, and a skin cosmetic using the same. A cosmetic base includes (A) 0.15-0.6 mass % of sodium acrylate-grafted starch and (B) 0.25-1.35 mass % of an associative thickener having a polyoxyalkylene chain wherein the total amount of the (A) sodium acrylate-grafted starch and (B) associative thickener having a polyoxyalkylene chain compounded is 0.5-1.5 mass % and to a skin cosmetic that uses the cosmetic base.

11 Claims, No Drawings

COSMETIC BASE AND SKIN COSMETIC USING SAME

CROSS REFERENCE TO RELATED APPLICATIONS

This application relates to and claims priority as a § 371 national phase, from PCT/JP2018/031890 filed Aug. 29, 2018, the entire contents of which are incorporated herein by reference, which in turn claims priority from PCT/JP2017/03338 filed Aug. 31, 2017.

TECHNICAL FIELD

The present invention relates to a cosmetic base giving a novel (unique) appearance and feeling on use (texture), and a skin cosmetic using such a base. More specifically, the present invention relates to a cosmetic base and skin cosmetic which have a sherbet-like appearance and can give a unique feel as if the cosmetic base (or cosmetic) collapses with allowing water to flow out, when applied to the skin.

BACKGROUND ART

In the technical field of cosmetics and external preparations for the skin, various thickeners are added in order to stabilize the preparation, regulate texture of the preparation, or to retain the dosage form. For example, Patent Document 1 discloses that an associative thickener composed of a relatively low molecular weight hydrophobically modified polyether urethane made of a water-soluble monomer and a hydrophobic monomer has excellent thickening stability against external factors such as salt concentration and pH, and has an excellent texture providing moist feeling.

Furthermore, Patent Document 2 discloses an emulsified cosmetic comprising a predetermined amount of a microgel prepared by pulverizing a gel made of a hydrophobically modified polyether urethane and a hydrophilic compound, and a powder and that such a cosmetic provides a loose (relaxing) feeling with imaging a sense of permeability when applied to the skin.

Meanwhile, sodium acrylate-grafted starch has been known as a hydrophilic (high water-absorbency) polymer, and a cosmetic containing sodium acrylate-grafted starch, in the form of mousse, has a unique, soft and light feeling on use and an excellent cool feeling (Patent Document 3). Furthermore, there is an example of a cosmetic, which contains a sodium acrylate-grafted starch (a block copolymer of starch and acrylic acid), a hydrophobically modified polyether urethane, and a water-swelling clay mineral in combination, and having an improved temperature stability of hardness (Patent Document 4). However, the object of the invention in Patent Document 4 is to maintain the hardness of a cosmetic above the predetermined hardness, and the cosmetic needs not only sodium acrylate-grafted starch and a hydrophobically modified polyether urethane, but also a water-swelling clay mineral in order to attain the object of the invention (Comparative Examples 5 and 6 in Patent Document 4). The cosmetics prepared as described above has a hardened texture.

CITATION LIST

Patent Literature

JP 2000-239120 A
JP 2014-40385 A
JP 2011-256154 A
JP 2015-30698 A

SUMMARY OF INVENTION

Technical Problem

In view of the above technical circumstances, an object of the present invention is to provide a cosmetic base having an unprecedented (unconventional) appearance and feeling on use, and particularly, to provide a cosmetic base with a novel (unknown) feeling on use along with providing a visual cool-feeling derived from the appearance thereof looking like a sherbet and a uniquely particular feeling as if the cosmetic per se softly bursts and loosens, i.e., collapses with allowing water to flow out, and a skin cosmetic using the base.

Solution to Problem

The present inventors have conducted intensive studies and, as a result, have found that the above unique appearance and feeling on use are obtained by incorporating a sodium acrylate-grafted starch and a specific thickener in combination and adjusting not only the respective amounts thereof but also the total amount thereof within specific ranges, and have completed the present invention, accordingly.

Specifically, the present invention provides:
a cosmetic base comprising:
(A) 0.15 to 0.6% by mass of sodium acrylate-grafted starch; and
(B) 0.25 to 1.35% by mass of an associative thickener having a polyoxyalkylene chain,
wherein the total amount of the sodium acrylate-grafted starch (A) and the associative thickener having a polyoxyalkylene chain (B) is 0.5 to 1.5% by mass, and further provides a skin cosmetic using the base.

Advantageous Effects of Invention

The cosmetic base of the present invention has a novel appearance and feeling on use that gives a visual cool-feeling by its sherbet-like appearance and a unique feel as if the cosmetic softly bursts and collapses (loosens) along with allowing water to flow out when applied to the skin. The cosmetic of the present invention is particularly suitable as a skin cosmetic.

DESCRIPTION OF EMBODIMENTS (A) Sodium Acrylate-Grafted Starch (INCI Name: Sodium Polyacrylate Starch)

The sodium acrylate-grafted starch (component A) in the cosmetic of the present invention is a sodium salt of starch to which acrylic acid has been graft-polymerized, and has been known as a high water-absorbency polymer and has been used as, for example, an adsorbent, a binder, an emulsion stabilizer or a hydrophilic thickener in the field of cosmetics.

The sodium acrylate-grafted starch in the present invention is not particularly limited, and commercially available products in the form of white particles may be used. Examples of commercially available products include MAKIMOUSSE 7 (average particle size is about 7 μm), MAKIMOUSSE 12 (average particle size is about 12 μm), MAKIMOUSSE 25 (average particle size is about 25 μm) and MAKIMOUSSE 400 (average particle size is about 400 μm) (manufactured by DAITO KASE KOGYO CO., LTD.) and Sanflesh ST-100C, ST100MC and IM-300MC (manufactured by Sanyo Chemical Industries, Ltd.).

High water-absorbency polymers in which the main chain is starch and to which acrylic polymer is grafted are also included in the sodium acrylate-grafted starch in the present invention. Examples of commercially available products of such polymers (INCI Name: starch/acrylamide/sodium acrylate copolymer) include Water Lock A-240, A-180, B-204, D-223, A-100, C-200 and D-223 (manufactured by Grain Processing Corporation).

The amount of the sodium acrylate-grafted starch (A) in the cosmetic base of the present invention is 0.15 to 0.6% by mass, preferably 0.15 to 0.55% by mass, and more preferably 0.2 to 0.55% by mass based on the total amount of the cosmetic base. When the amount is less than 0.15% by mass, the sherbet-like appearance cannot be obtained. The lower limit of the amount can be any value within the above-specified range, for example, 0.16% by mass or more, 0.17% by mass or more, 0.18% by mass or more, 0.19% by mass or more, or 0.20% by mass or more. When the amount is more than 0.6% by mass, feeling on use may be slimy. The upper limit of the amount can be any value within the above-specified range, for example, 0.54% by mass or less, 0.53% by mass or less, 0.52% by mass or less, 0.51% by mass or less, 0.50% by mass or less, or 0.49% by mass or less.

(B) Associative Thickener Having Polyoxyalkylene Chain

The component (B) in the present invention is an associative thickener having a polyoxyalkylene chain in its molecule. The "associative thickener" is a copolymer having a hydrophilic portion made from a water-soluble monomer and a hydrophobic portion made from a hydrophobic monomer, and as a hydrophobic interaction causes association in an aqueous solvent, the copolymer acts as if it is a physically cross-linked macromolecule, and thus has an action of thickening the system (see, for example, paragraph [0014] in the above Patent Document 1).

The component (B) in the present invention is an associative thickener having a polyoxyalkylene chain as a hydrophilic portion. Examples of polyoxyalkylene chains include, but are not limited to, polyoxyethylene chain, polyoxypropylene chain and polyoxybutylene chain.

In the present description, the component (B) may be hereinafter simply referred to as an "associative thickener."

It is preferable that the associative thickener (component (B)) in the present invention is at least one selected from the group consisting of (B-1) a hydrophobically modified polyether urethane, (B-2) a hydrophobically modified alkylcellulose and (B-3) a polyacrylate crosspolymer. In the present invention, any one of (B-1) the hydrophobically modified polyether urethane, (B-2) the hydrophobically modified alkylcellulose and (B-3) the polyacrylate crosspolymer can be used, or two or more of them can be formulated in combination.

(B-1) Hydrophobically Modified Polyether Urethane

A hydrophobically modified polyether urethane represented by the following formula (I) is preferred as the hydrophobically modified polyether urethane (component B-1) used in the cosmetic base of the present invention.

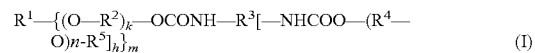

In the above formula (I), $R^1$, $R^2$ and $R^4$ each independently represent an alkylene group having 2 to 4 carbon atoms or a phenyl ethylene group. They are preferably an alkylene group having 2 to 4 carbon atoms.

$R^3$ represents an alkylene group having 1 to 10 carbon atoms and optionally having a urethane bond.

$R^5$ represents a linear, branched or secondary alkyl group having 8 to 36, preferably 12 to 24 carbon atoms.

Wherein, m is a number of 2 or more, and preferably 2. Wherein, h is a number of 1 or more, and preferably 1. Wherein, k is a number of 1 to 500, and preferably a number of 100 to 300. Wherein, n is a number of 1 to 200, and preferably a number of 10 to 100.

Examples of particularly preferred hydrophobically modified polyether urethanes in the present invention include a (PEG-240/decyltetradeces-20/HDI) copolymer (a copolymer represented by the above formula (I), wherein $R^1$=an ethyl group, $R^2$ and $R^4$ are each an ethylene group, $R^3$=a hexamethylene group, $R^5$=a 2-dodecyl tetradecyl group, h=1, m=2, k=120, n=20). This copolymer is commercially available from ADEKA Corporation with the product name "ADEKANOL GT700" or "ADEKANOL GT730."

(B-2) Hydrophobically Modified Alkylcellulose

It is preferable that (B-2) the hydrophobically modified alkylcellulose used in the present invention is one represented by the formula (II).

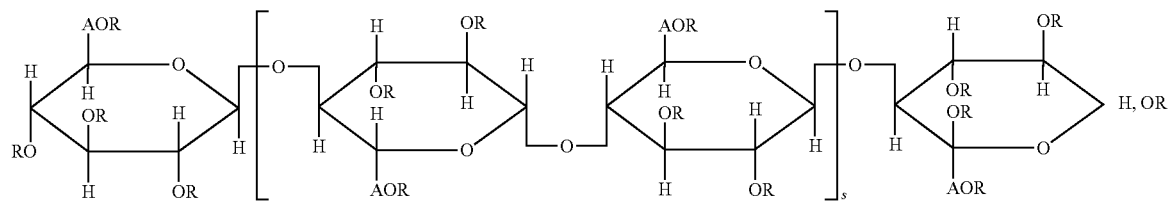

In the above formula (II), R is a bonded (composite) group $R_1$-$R_2$, $R_1$ is the same or different in the molecule, and is a group selected from —[$CH_2CH(CH_3)O$]$_r$—, —[$CH_2CH_2$]$_r$— and —[$CH_2CH(OH)CH_2$]$_r$— (wherein r is an integer of 0 to 4), $R_2$ is at least one group selected from a hydrocarbon group having 12 to 28 carbon atoms (preferably an alkyl group having 1 to 4 carbon atoms) and a hydrogen atom, and at least one $R_2$ in a molecule is a hydrocarbon group having 12 to 28 carbon atoms (preferably an alkyl group having 1 to 4 carbon atom). A is a group —($CH_2$)$_t$— (wherein t is an integer of 1 to 3) and s is a number of 100 to 10,000.

The hydrophobically modified alkylcellulose of the formula (II) has a structure in which a long chain alkyl group, which is a hydrophobic group, is introduced into a water-soluble cellulose ether derivative through a polyoxyalkylene chain. Examples of water-soluble cellulose ether derivatives, which are the base of the molecule, include methylcellulose, ethyl cellulose, propyl cellulose, butyl cellulose, hydroxyethyl cellulose, Hydroxypropylcellulose and hydroxypropyl methylcellulose. The hydrophobically modified alkylcellulose may be prepared by reacting those with long chain alkyl glycidyl ether (e.g., those represented by the following formula (II')).

In the formula (II'), R' is an alkyl group having 10 to 28, preferably 12 to 22 carbon atoms.

Hydroxypropyl methylcellulose or hydroxyethyl cellulose are preferred as the above water-soluble cellulose ether derivative. In particular, it is preferable to select hydroxypropyl methylcellulose. Furthermore, it is preferable that R' in long chain alkyl glycidyl ether (II') is a stearyl group ($—C_{18}H_{37}$) or a cetyl group ($—C_{16}H_{33}$) (in these cases, $—CH_2CH(OH)CH_2OR'$ is $—CH_2CH(OH)CH_2O—C_{18}H_{37}$ or $—CH_2CH(OH)CH_2O—C_{16}H_{33}$).

The most preferred form of the hydrophobically modified alkylcellulose (component B-2) is stearoxy hydroxypropyl methylcellulose (INCI name: Hydroxypropylmethylcellulose Stearoxy Ether) in which the hydrophobic group R' in the formula (II') is a stearyl group. A product with the product name "SANGELOSE" commercially available from Daido Chemical Corporation may also be used. (Product names: SANGELOSE 90L, 90M, 90H, 60L, 60M, 60H and the like).

(B-3) Polyacrylate Crosspolymer

The polyacrylate crosspolymer (component B-3) used in the present invention is preferably a crosspolymer in which the polyacrylate main chain is crosslinked with a polyoxyalkylene chain. The polyacrylate main chain may have various substituents (side chains) as long as the polyacrylate crosspolymer is used as an associative thickener.

Particularly preferred examples of polyacrylate crosspolymers (component B-3) may include polyacrylate crosspolymer-6 (INCI name). Polyacrylate crosspolymer-6 is prepared by cross-linking a copolymer of acryloyldimethyltaurine ammonium, dimethylacrylamide, lauryl methacrylate and laureth-4 methacrylate with trimethylolpropane triacrylate. A product with the product name "SEPIMAX ZEN" commercially available from SEPPIC, for example, may be used.

The amount of the associative thickener (B) in the present invention is 0.25 to 1.35% by mass, preferably 0.25 to 1.0% by mass, more preferably 0.25 to 0.8% by mass, and most preferably 0.3 to 0.8% by mass based on the total amount of the cosmetic base. When the amount is less than 0.25% by mass, the unique feeling on use of the present invention cannot be achieved. The lower limit of the amount can be any value within the above-specified range, for example, 0.26% by mass or more, 0.27% by mass or more, 0.28% by mass or more, 0.29% by mass or more, or 0.30% by mass or more. When more than 1.35% by mass of the associative thickener (B) is formulated, the cosmetic is likely to be sticky. The upper limit of the amount can be any value within the above-specified range, for example, 1.30% by mass or less, 1.20% by mass or less, 1.10% by mass or less, 1.00% by mass or less, 0.80% by mass or less, or 0.70% by mass or less.

In the cosmetic base of the present invention, the respective amounts of sodium acrylate-grafted starch (A) and an associative thickener (B) are specified as described above, and the total amount of both (A) and (B) is limited to the range of 0.5 to 1.5% by mass, and thus a unique appearance and a unique feeling on use are achieved. The upper limit of the total amount is more preferably 1.3% by mass or less, further preferably 1.2% by mass or less, and most preferably 1.0% by mass or less. The lower limit of the total amount is preferably 0.55% by mass or more, more preferably 0.6% by mass or more, and further preferably 0.7% by mass or more.

The cosmetic base of the present invention looks like a sherbet and a feeling on use thereof is as if the cosmetic collapses (loosens) with allowing water to flow out, and thus it is preferable that the cosmetic base is formulated as a skin cosmetic taking advantage from such characteristics. Thus, the present invention also relates to a skin cosmetic containing the above cosmetic base.

The "feeling on use as if water is flowing out" in the present description means that the cosmetic is a sherbet-like coating agent without such a sensation of overflowing water immediately after being applied and then, spreading of water on the skin along with the sensation as water comes out of the cosmetic when the cosmetic is pressed with a finger or a hand.

Meanwhile, the "appearance (look) like a sherbet" in the present invention means that although the cosmetic itself does not actually contain ice, the appearance reminds a user of sherbet in which ice and water is mixed to make a frozen smoothie. With such an appearance of the cosmetic, users expect a cool feeling on application. For example, the cosmetic is refrigerated or frozen, and then when the cooled cosmetic is applied to the skin which has been exposed to the sunlight in summer or in which one feels fatigue is accumulated, a user can actually feel the cool feeling expected from the appearance and can feel much satisfaction caused by the fresh feeling of use.

It is preferable that the skin cosmetic using the base of the present invention is in the form of an aqueous cosmetic in consideration of its characteristics. The "aqueous skin cosmetic" in the present description means a skin cosmetic in which the amount of an oil component is about 20% by mass or less. In some cases the amount of the oil component may be 15% by mass or less, 10% by mass or less, 8% by mass or less, or 5% by mass or less, and this achieves very light feeling on use. Furthermore, the amount of the oil component may be reduced to 3% by mass or less, or a cosmetic without an oil component may be prepared.

When an oil component is comprised, the lower limit of the amount is not particularly limited, and is, for example, 0.01% by mass or more, 0.1% by mass or more, 0.5% by mass or more, or 1.0% by mass or more. The form of the aqueous skin cosmetic according to the present invention is not particularly limited, and may be, for example, an aqueous solution, an oil-in-water emulsion and a water-in-oil-in-water emulsion.

The oil component which can be formulated in the skin cosmetic of the present invention may be one or more components selected from liquid oil and fat, solid or semi-solid oil and fat, hydrocarbon oil, higher fatty acid, higher alcohol, ester oil, silicone oil and the like, which are conventionally used in a skin cosmetic, and is not particularly limited.

Specific examples thereof include liquid oils and fats such as avocado oil, camellia oil, macadamia nut oil, mink oil, olive oil, castor oil, jojoba oil, triglycerol and glycerol trioctanoate, hydrocarbon oils such as liquid paraffin, squalane, paraffin, ceresin and squalene, higher fatty acids such as lauric acid, myristic acid, palmitic acid, stearic acid, behenic acid, oleic acid, 12-hydroxystearic acid, isostearic acid, linoleic acid and linolenic acid, higher alcohols such as lauryl alcohol, cetyl alcohol, stearyl alcohol, behenyl alcohol, oleyl alcohol, monostearyl glycerol ether, monopalmityl glycerol ether, cholesterol, phytosterol and isostearyl alcohol, ester oils such as coco-caprylate, isononyl isononanoate, isopropyl myristate, cetyl octanoate, octyldodecyl myristate, butyl stearate, decyl oleate, ethylene glycol dioctanoate, diisostearyl malate, trimethylolpropane trioctanoate, trimethylolpropane triisostearate, pentaerythritol tetraoctanoate, glycerol trioctanoate, glycerol triisostearate, ethyl acetate, butyl acetate and amyl acetate, linear silicone oils such as dimethyl polysiloxane, methylphenyl polysiloxane, methyl hydrogen polysiloxane and diphenylsiloxyphenyl trimethicone, cyclic silicone oils such as decamethylcyclopentasiloxane, dodecamethylcyclohexasiloxane and octamethylcyclotetrasiloxane, and oils and fats which are solid or semi-solid at room temperature, such as beeswax, candelilla wax, cotton wax, carnauba wax, bayberry wax, insect wax, spermaceti, montan wax, bran wax, lanolin, kapok wax, Japan wax, lanolin acetate, liquid lanolin, sugarcane wax, lanolin fatty acid isopropyl, hexyl laurate, reduced lanolin, jojoba wax, hard lanolin, shellac wax, beeswax, microcrystalline wax, paraffin wax, POE lanolin alcohol ether, POE lanolin alcohol acetate, POE cholesterol ether, lanolin fatty acid polyethylene glycol, fatty acid glyceride, hydrogenated castor oil, Vaseline® (petrolatum) and POE hydrogenated lanolin alcohol ether.

Examples of silicone oils include a linear, branched or cyclic silicone oil, such as dimethicone, phenyl dimethicone, amino-modified silicone oil and alkyl-modified silicone oil.

When an oil component is comprised, it is preferable to comprise a surfactant which emulsifies the oil component. The surfactant used in the present invention is not particularly limited as long as it can be used in cosmetics. In particular, a hydrophilic non-ionic surfactant having an HLB of 7 or more, preferably 10 or more, is preferably used.

Furthermore, the cosmetic of the present invention may contain other components conventionally used in cosmetics and external preparations for the skin, such as an ultraviolet absorber, a moisturizing agent, a perfume, various pharmaceutically active ingredients, an antiseptic, an antioxidant, a powder and a color material, as necessary, within the range that does not impair the effect of the present invention.

For example, the skin cosmetic of the present invention containing a lower alcohol (alcohol having 1 to 6 carbon atoms) such as ethanol has further improved cool feeling and refreshing feeling when the cosmetic is applied to the skin. Since the skin cosmetic of the present invention contains both hydrophobically modified polyether urethane and sodium acrylate-grafted starch, no reduction of viscosity occurs even when alcohol is also present.

Furthermore, the skin cosmetic of the present invention containing a silicone elastomer can further have suppressed stickiness after application and can maintain a smooth touch (sensation).

The cosmetic of the present invention may also be provided in the form of a coloring cosmetic containing a color material such as pigment and coloring. Examples of color materials include inorganic white pigments (e.g., pigment grade titanium oxide and zinc oxide); particulate metal oxides (e.g., particulate titanium oxide, particulate zing oxide); inorganic red pigments (e.g., iron titanate); inorganic purple pigments (e.g., mango violet, cobalt violet); inorganic green pigments (e.g., chrome oxide, chrome hydroxide, cobalt titanate); inorganic blue pigments (e.g., ultramarine, iron blue); pearl pigments (e.g., titanium oxide coated mica, titanium oxide coated bismuth oxychloride, titanium oxide coated talc, colored titanium oxide coated mica, bismuth oxychloride, argentine); red iron oxide, yellow iron oxide, black iron oxide, carbon black; metal powder pigments (e.g., aluminum powder, copper powder); organic pigments such as zirconium, barium and aluminum lake (e.g., Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, Blue No. 404, Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3 and Blue No. 1); natural pigments (e.g., chlorophyll, 3-carotene). One of them may be used, or two or more of them may be used in combination.

When the cosmetic of the present invention contains a pigment as a color material, precipitation of pigment powder is suppressed by incorporating an aqueous thickener (other than the above component (A) or component (B)) and as a result, stability is improved. Examples of aqueous thickeners include plant-based polymers such as agar, xanthan gum, gum Arabic, carrageenan, pectin, quince seed (*Cydonia oblonga*) and algae colloid (brown algae extract), microorganism-based polymers such as dextran and pullulan, animal-based polymers such as collagen, casein and gelatin, alginic acid-based polymers such as sodium alginate, vinyl polymers such as carboxyvinyl polymer (e.g., CARBOPOL®), acrylic polymers such as sodium polyacrylate and polyacrylamide, and inorganic water-soluble polymers such as bentonite, aluminum magnesium silicate and laponite. Using, of these water-soluble thickeners, agar and particulate agar prepared by pulverizing an aqueous gel optionally containing another aqueous thickener is effective.

The aqueous thickener is effective for stabilization not only when the cosmetic contains a pigment but also an inorganic powder (e.g., talc, kaolin, sericite, muscovite, synthetic mica, phlogopite, lepidolite, biotite, lithia mica, vermiculite, magnesium carbonate, calcium carbonate, diatomaceous earth, magnesium silicate, calcium silicate, aluminum silicate, barium silicate, strontium silicate, metal tungstate, silica, hydroxyapatite, zeolite, boron nitride, ceramics powder) and/or an organic powder (e.g., PMMA (poly(methylmethacrylate)) powder, nylon powder) is contained.

The skin cosmetic of the present invention is in the form of a gel having a sherbet-like appearance. The cosmetic has a viscosity at 30° C. of 5,000 mPa·s or more, preferably 10,000 mPa·s or more, and more preferably 20,000 mPa·s or more as measured by a B-type viscometer. The upper limit of the viscosity is 250,000 mPa·s or less, preferably 200,000 mPa·s or less, and more preferably 150,000 mPa·s or less.

Thus, the amount of the water-soluble polymer such as agar is 0.5% by mass or less, and preferably 0.4% by mass or less.

The skin cosmetic of the present invention can be prepared by a method which has been conventionally used. For example, the skin cosmetic may be prepared by mixing aqueous components, powder components and oil components separately, and adding the powder components and the oil components to the aqueous components and stirring the mixture.

The skin cosmetic of the present invention is suitable for being provided in the form of an aqueous cosmetic for, in particular, the face or the body.

EXAMPLES

Hereinafter the present invention will be described in more detail with reference to Examples, but the present invention is not limited to these Examples. The amount is in % by mass unless otherwise specified.

Skin cosmetics (samples) were prepared based on the formulation shown in the following table. The samples of Examples were evaluated for the following items. The results are also shown in the table.

<Appearance that Reminds Users of Cool Feeling (Sherbet-Like Appearance)>

<Unique Feeling on Use as if Cosmetic Collapses to Allow Water to Flow Out (Water Collapsing Feeling)>

Expert panelists (10 women) used the respective samples (compositions) and evaluated if they feel a cool feeling from the sherbet-like appearance and if they feel the novel and unique feeling on use of the present invention when the sample was applied to the skin, according to the following criteria.

(Criteria for Evaluation)

$A^+$: 9 or more panelists out of 10 responded "Yes, I feel".
A: 8 or more panelists out of 10 responded "Yes, I feel".
B: 5 to 7 panelists out of 10 responded "Yes, I feel".
C: 3 to 4 panelists out of 10 responded "Yes, I feel".
D: 2 or less panelists out of 10 responded "Yes, I feel".

In addition to the above, "refreshing feeling when applied," "no stickiness after application," "smudging of cosmetic" and "moisturizing feel on the skin" were evaluated according to the same criteria.

TABLE 1

|  | Comparative Example1-1 | Comparative Example1-2 | Example 1-1 | Example 1-2 | Example 1-3 | Comparative Example1-3 |
|---|---|---|---|---|---|---|
| Ion exchanged water | Balance | Balance | Balance | Balance | Balance | Balance |
| Ethanol | 5 | 5 | 5 | 5 | 5 | 5 |
| Glycerol | 1 | 1 | 1 | 1 | 1 | 1 |
| 1,3-Butylene glycol | 5 | 5 | 5 | 5 | 5 | 5 |
| (PEG-240/decyltetradeces-20/HDI) copolymer | — | 0.1 | 0.5 | 0.5 | 0.5 | 0.5 |
| Sodium acrylate-grafted starch | 0.5 | 0.5 | 0.35 | 0.5 | 0.2 | — |
| Phenoxyethanol | 0.5 | 0.5 | 0.5 | 0.5 | 0.5 | 0.5 |
| EDTA-2Na•2H$_2$O | 0.03 | 0.03 | 0.03 | 0.03 | 0.03 | 0.03 |
| Total | 100 | 100 | 100 | 100 | 100 | 100 |
| Viscosity (mPa · s/30° C.) | 14100 | 22700 | 42600 | 118000 | 35350 | 1100 |
| Sherbet-like appearance | C | C | $A^+$ | $A^+$ | $A^+$ | D |
| Water collapsing feeling | D | D | $A^+$ | $A^+$ | $A^+$ | D |

As shown in Table 1, in Examples 1-1 to 1-3 in which the amount of the sodium acrylate-grafted starch (A) and the amount of the associative thickener (B) ((PEG-240/decyltetradeces-20/HDI) copolymer) and the total amount of the two satisfy the requirement of the present invention, the rating for the sherbet-like appearance and the rating for the water collapsing feeling were "$A^+$," showing that almost all the panelists actually found the excellent appearance (sherbet-like appearance) and touch (water collapsing feeling). On the other hand, nether excellent appearance nor touch was found in Comparative Examples 1-1 and 1-3, which did not contain either the sodium acrylate-grafted starch (A) or the associative thickener (B) ((PEG-240/decyltetradeces-20/HDI) copolymer), and in Comparative Example 1-2 in which the amount of the associative thickener (B) was out of the range of the present invention.

Samples prepared by changing the amount of the associative thickener (B) ((PEG-240/decyltetradeces-20/HDI) copolymer) and the sodium acrylate-grafted starch (A) in the above formulation of Example 1-1 were evaluated in the same manner. The results are shown in the following Tables 2-1, 2-2 and 2-3.

TABLE 2-1

| No. | 2-1 | 2-2 | 2-3 | 2-4 | 2-5 | 2-6 | 2-7 | 2-8 | 2-9 | 2-10 |
|---|---|---|---|---|---|---|---|---|---|---|
| (A): Sodium acrylate-grafted starch | 0.2 | 0.5 | 0.2 | 0.3 | 1 | 0.35 | 0.45 | 0.5 | 0.55 | 0.35 |
| (B): PEG-240/decyltetradeces-20/HDI copolymer | 0.1 | 0.1 | 0.2 | 0.2 | 0.2 | 0.3 | 0.3 | 0.3 | 0.3 | 0.35 |
| Total of (A) + (B) | 0.3 | 0.6 | 0.4 | 0.5 | 1.2 | 0.65 | 0.75 | 0.8 | 0.85 | 0.7 |
| Sherbet-like appearance | C | C | C | C | C | A | $A^+$ | $A^+$ | $A^+$ | $A^+$ |
| Water collapsing feeling | C | C | C | C | C | A | $A^+$ | $A^+$ | $A^+$ | $A^+$ |

TABLE 2-2

| No. | 2-11 | 2-12 | 2-13 | 2-14 | 2-15 | 2-16 | 2-17 | 2-18 | 2-19 | 2-20 |
|---|---|---|---|---|---|---|---|---|---|---|
| (A): Sodium acrylate-grafted starch | 0.45 | 0.5 | 0.2 | 0.35 | 0.5 | 0.2 | 0.3 | 0.2 | 0.5 | 0.2 |
| (B): PEG-240/decyltetradeces-20/HDI) copolymer | 0.4 | 0.4 | 0.5 | 0.5 | 0.5 | 0.75 | 0.75 | 0.8 | 0.8 | 1 |
| Total of (A) + (B) | 0.85 | 0.9 | 0.7 | 0.85 | 1 | 0.95 | 1.05 | 1 | 1.3 | 1.2 |
| Sherbet-like appearance | $A^+$ | $A^+$ | $A^+$ | $A^+$ | $A^+$ | $A^+$ | B | $A^+$ | B | B |
| Water collapsing feeling | $A^+$ | $A^+$ | $A^+$ | $A^+$ | $A^+$ | $A^+$ | B | $A^+$ | B | B |

TABLE 2-3

| No. | 2-21 | 2-22 | 2-23 | 2-24 | 2-25 | 2-26 | 2-27 | 2-28 |
|---|---|---|---|---|---|---|---|---|
| (A): Sodium acrylate-grafted starch | 0.5 | 0.12 | 0.5 | 1.0 | 1.0 | 1.0 | 0.6 | 0.1 |
| (B): PEG-240/decyltetradeces-20/HDI) copolymer | 1 | 1.4 | 1.4 | 0.5 | 1.0 | 1.5 | 1.5 | 1.5 |
| Total of (A) + (B) | 1.5 | 1.52 | 1.9 | 1.5 | 2 | 2.5 | 2.1 | 1.6 |
| Sherbet-like appearance | B | C | C | C | C | C | C | C |
| Water collapsing feeling | B | C | C | C | C | C | C | C |

As shown in Tables 2-1 to 2-3, when the amount of the sodium acrylate-grafted starch (A) and the amount of the associative thickener (B) ((PEG-240/decyltetradeces-20/HDI) copolymer) and the total amount of the two satisfy the requirement of the present invention, the rating for the sherbet-like appearance and the rating for the water collapsing feeling were "B" or higher, showing that more than half of the panelists evaluated the samples as having an excellent appearance and touch. In particular, when the total amount is 1% by mass or less, almost all panelists rated the samples as having an excellent appearance and touch ($A^+$ or A). On the other hand, in the case of samples which did not satisfy the requirement of the present invention, the result of evaluation was "C," and less than half of the panelists felt the excellent appearance and touch.

Next, samples prepared by replacing the associative thickener (B) with (B-2) a hydrophobically modified alkylcellulose or (B-3) polyacrylate crosspolymer were evaluated in the same manner. The results are shown in Table 3.

TABLE 3

| | Example 3-1 | Example 3-2 | Example 3-3 | Example 3-4 | Example 3-5 | Example 3-6 |
|---|---|---|---|---|---|---|
| Ion exchanged water | Balance | Balance | Balance | Balance | Balance | Balance |
| Ethanol | 5 | 5 | 5 | 5 | 5 | 5 |
| Glycerol | 1 | 1 | 1 | 1 | 1 | 1 |
| 1,3-Butylene glycol | 5 | 5 | 5 | 5 | 5 | 5 |
| Sodium acrylate-grafted starch | 0.35 | 0.35 | 0.35 | 0.35 | 0.35 | 0.35 |
| Stearoxy hydroxypropyl cellulose | 0.3 | 0.5 | 0.7 | — | — | — |
| Polyacrylate crosspolymer-6 | — | — | — | 0.3 | 0.5 | 0.7 |
| Phenoxyethanol | 0.5 | 0.5 | 0.5 | 0.5 | 0.5 | 0.5 |
| EDTA-2Na•2H$_2$O | 0.03 | 0.03 | 0.03 | 0.03 | 0.03 | 0.03 |
| Total | 100 | 100 | 100 | 100 | 100 | 100 |
| Sherbet-like appearance | $A^+$ | $A^+$ | $A^+$ | $A^+$ | $A^+$ | $A^+$ |
| Water collapsing feeling | A | A | A | $A^+$ | $A^+$ | A |

As shown in Table 3, even for the samples prepared by replacing the associative thickener (B) with (B-2) hydrophobically modified alkylcellulose (Stearoxy hydroxypropyl cellulose) or (B-3) polyacrylate crosspolymer-6, almost all panelists felt the excellent appearance and touch equivalent to those of the samples prepared by using hydrophobically modified polyether urethane.

Next, the influence of optional components in the present invention on the cosmetic base and the cosmetic of the present invention was investigated. The results are shown in the following Tables 4 to 7.

TABLE 4

| | Example 4-1 | Example 4-2 | Comparative Example 4-1 | Comparative Example 4-2 | Comparative Example 4-3 | Comparative Example 4-4 |
|---|---|---|---|---|---|---|
| Ion exchanged water | Balance | Balance | Balance | Balance | Balance | Balance |
| Ethanol | 5 | 10 | 5 | 10 | 5 | 10 |
| Glycerol | 1 | 1 | 1 | 1 | 1 | 1 |
| 1,3-Butylene glycol | 5 | 5 | 5 | 5 | 5 | 5 |
| (PEG-240/decyltetradeces-20/HDI) copolymer | 1 | 1 | 1 | 1 | 1 | 1 |
| Sodium acrylate-grafted starch | 0.35 | 0.35 | — | — | — | — |
| PEG-9 polydimethylsiloxyethyl dimethicone (*1) | 0.3 | 0.3 | 0.3 | 0.3 | — | — |
| Dimethicone (*2) | 2 | 2 | 2 | 2 | — | — |
| Highly polymerized dimethylsiloxane - methyl(aminopropyl)siloxane copolymer (10%), methyl polysiloxane (90%) (*3) | 0.3 | 0.3 | 0.3 | 0.3 | — | — |
| Diphenylsiloxy phenyl trimethicone (*4) | 1 | 1 | 1 | 1 | — | — |
| Phenoxyethanol | 0.5 | 0.5 | 0.5 | 0.5 | 0.5 | 0.5 |
| EDTA-2Na•2H$_2$O | 0.03 | 0.03 | 0.03 | 0.03 | 0.03 | 0.03 |
| Total | 100 | 100 | 100 | 100 | 100 | 100 |
| Viscosity (mPa · s/30° C.) | 134400 | 130000 | 6900 | 2800 | 10600 | 2900 |
| Viscosity after stored at 50° C. | 98800 | 82000 | 1470 | 510 | 1270 | 500 |
| Sherbet-like appearance | A$^+$ | A$^+$ | D | D | D | D |
| Water collapsing feeling | A$^+$ | A$^+$ | D | D | D | D |
| Refreshing feeling (cool feeling) | A | A$^+$ | D | D | D | D |
| Stability | Good | Good | Separated | Separated | — | — |

(*1): Silicone SC0938B (manufactured by Shin-Etsu Chemical Co., Ltd.)
(*2): Silicone KF-96A-6T (manufactured by Shin-Etsu Chemical Co., Ltd.)
(*3): APS-10-DMS (manufactured by Shin-Etsu Chemical Co., Ltd.)
(*4): Silicone KF56 (manufactured by Shin-Etsu Chemical Co., Ltd.)

In the samples of the present invention which contained a predetermined amount of sodium acrylate-grafted starch (A) and an associative thickener (B), refreshing feeling (cool feeling) was obtained without a significant reduction in viscosity or instability caused by containing of ethanol (Examples 4-1, 4-2). On the other hand, in Comparative Examples 4-1 and 4-2 which did not contain the sodium acrylate-grafted starch (A), the viscosity significantly decreased after being stored at 50° C. for 3 days, and even separation of the emulsion was observed. Other results confirm that the decrease in the viscosity was not caused by other oil components (Comparative Examples 4-3, 4-4).

TABLE 5

| | Example 5-1 | Example 5-2 | Example 5-3 | Example 5-4 |
|---|---|---|---|---|
| Ion exchanged water | Balance | Balance | Balance | Balance |
| Ethanol | 5 | 10 | 10 | 10 |
| Glycerol | 1 | 1 | 1 | 1 |
| 1,3-Butylene glycol | 5 | 5 | 5 | 5 |
| (PEG-240/decyltetradeces-20/HDI) copolymer | 0.5 | 0.35 | 0.35 | 0.5 |
| Sodium acrylate-grafted starch | 0.35 | 0.5 | 0.5 | 0.35 |
| PEG-9 polydimethylsiloxyethyl dimethicone (*1) | 0.3 | 0.3 | 0.3 | 0.3 |
| Dimethicone (*2) | 2 | 2 | — | 1 |
| Dimethicone (*5) | — | — | 3 | 3 |
| Diphenylsiloxy phenyl trimethicone (*4) | 1 | 1 | — | — |
| Highly polymerized dimethylsiloxane - methyl(aminopropyl)siloxane copolymer (10%), methyl polysiloxane (90%) (*3) | 0.3 | 0.3 | 0.3 | 0.3 |
| Phenoxyethanol | 0.5 | 0.5 | 0.5 | 0.5 |
| EDTA-2Na•2H2O | 0.03 | 0.03 | 0.03 | 0.03 |
| Total | 100 | 100 | 100 | 100 |
| Viscosity (mPa · s/30° C.) | 52800 | 57500 | 60200 | 61000 |
| pH | 7.00 | 6.98 | 6.99 | 7.00 |
| Emulsified particles | 1-7.5 (12.5) | 1-7.5 (12.5) | 1-7.5 (12.5) | 1-7.5 (12.5) |
| Sherbet-like appearance | A$^+$ | A$^+$ | A$^+$ | A$^+$ |
| Water collapsing feeling | A$^+$ | A$^+$ | A$^+$ | A$^+$ |
| No stickiness after application | B | A | A | A$^+$ |
| Smudging of cosmetic | A | B | B | A |

(*1) to (*4): same as in Table 4
(*5): KF-96L-1.5cs (manufactured by Shin-Etsu Chemical Co., Ltd.)

These results confirm that the sherbet-like appearance and the water collapsing feeling, which are the advantageous effects of the present invention, have been obtained in the samples of the present invention which contain a predetermined amount of sodium acrylate-grafted starch (A) and an associative thickener (B), even when the type of the oil component was changed. The degree of stickiness or smudging of the cosmetic after application slightly varied depending on the type of the oil component, but was negligible.

TABLE 6

| | Example 6-1 | Example 6-2 | Example 6-3 | Example 6-4 |
|---|---|---|---|---|
| Ion exchanged water | Balance | Balance | Balance | Balance |
| Ethanol | 5 | 5 | 5 | 5 |
| Glycerol | 1 | 1 | 1 | 1 |

TABLE 6-continued

|  | Example 6-1 | Example 6-2 | Example 6-3 | Example 6-4 |
|---|---|---|---|---|
| 1,3-Butylene glycol | 5 | 5 | 5 | 5 |
| (PEG-240/decyltetradeces-20/HDI) copolymer | 0.5 | 0.5 | 0.5 | 0.5 |
| Sodium acrylate-grafted starch | 0.35 | 0.35 | 0.35 | 0.35 |
| PEG-9 polydimethylsiloxyethyl dimethicone (*1) | 0.3 | 0.3 | 0.3 | 1 |
| Dimethicone (*2) | 2 | 4 | 7 | 7 |
| Diphenylsiloxy phenyl trimethicone (*4) | 1 | 1 | 1 | 1 |
| Highly polymerized dimethylsiloxane - methyl(aminopropyl)siloxane copolymer (10%), methyl polysiloxane (90%) (*3) | 0.3 | 0.3 | 0.3 | — |
| Methylpolysiloxane (84.0%), alkyl cross-linked polydimethylsiloxane (16.0%) (*6) | — | — | — | 10 |
| Phenoxyethanol | 0.5 | 0.5 | 0.5 | 0.5 |
| EDTA-2Na•2H2O | 0.03 | 0.03 | 0.03 | 0.03 |
| Total | 100 | 100 | 100 | 100 |
| Viscosity (mPa · s/30° C.) | 52800 | 51000 | 53100 | 50100 |
| Sherbet-like appearance | A+ | A+ | A+ | A+ |
| Water collapsing feeling | A+ | A+ | A+ | A+ |
| No stickiness after application | A | A+ | A+ | A+ |
| Moisturizing feel | A | A | A | A+ |

(*1) to (*4): same as in Table 4
(*6): DOW CORNING(R) 9041 SILICONE ELASTOMER BLEND (manufactured by Dow Corning Toray, Co., Ltd.)

These results confirm that the sherbet-like appearance and the water collapsing feeling, which are the advantageous effects of the present invention, have been obtained in the samples of the present invention which contain a predetermined amount of sodium acrylate-grafted starch (A) and an associative thickener (B), even when the type and/or the amount of the oil component were changed. When the amount of low viscosity linear silicone oil (Silicone KF-96A-6T), an oil component, was increased, stickiness after application was further suppressed (Examples 6-2 and 6-3). When a silicone elastomer was contained, "moisturizing" feel improved.

TABLE 7

|  | Example 7-1 | Example 7-2 | Example 7-3 | Example 7-4 |
|---|---|---|---|---|
| Ion exchanged water | Balance | Balance | Balance | Balance |
| Ethanol | 5 | 5 | 5 | 5 |
| Glycerol | 1 | 1 | 1 | 1 |
| 1,3-Butylene glycol | 5 | 5 | 5 | 5 |
| (PEG-240/decyltetradeces-20/HDI) copolymer | 0.5 | 0.5 | 0.5 | 0.5 |
| Sodium acrylate-grafted starch | 0.35 | 0.35 | 0.35 | 0.35 |
| PEG-9 polydimethylsiloxyethyl dimethicone (*1) | 0.3 | 0.3 | — | — |
| Polyoxyethylene(20) polyoxypropylene(8) cetyl ether | — | — | — | 0.2 |
| PEG-60 glyceryl isostearate | — | — | — | 0.2 |
| PEG-60 hydrogenated castor oil | — | — | 0.2 | — |
| Dimethicone (*2) | 1 | 1 | 1 | — |
| Highly polymerized dimethylsiloxane - methyl(aminopropyl)siloxane copolymer (10%), methyl polysiloxane (90%) (*3) | 0.3 | 0.3 | 0.3 | 0.4 |
| Pentaerythritol tetraethylhexanoate | 4 | — | — | — |
| Hydrogenated polydecene | — | 4 | 4 | 8.5 |
| Phenoxyethanol | 0.5 | 0.5 | 0.5 | 0.5 |
| EDTA-2Na•2H2O | 0.03 | 0.03 | 0.03 | 0.03 |
| Total | 100 | 100 | 100 | 100 |
| Viscosity (mPa · s/30° C.) | 54000 | 53000 | 54600 | 53300 |
| Sherbet-like appearance | A+ | A+ | A+ | A+ |
| Water collapsing feeling | A+ | A+ | A+ | A+ |
| No stickiness after application | A | A+ | A+ | A+ |
| Moisturizing feel | A+ | A+ | A+ | A+ |

(*1) to (*3): same as in Table 1

These results confirm that the sherbet-like appearance and the water collapsing feeling, which are the advantageous effects of the present invention, have been obtained in the samples of the present invention which contain a predetermined amount of sodium acrylate-grafted starch (A) and an associative thickener (B), even when the type of the oil component and/or the surfactant were changed. All samples have no stickiness after application and gives an excellent moisturizing feel.

A cosmetic (cosmetic A) colored by a pigment powder was prepared with the formulation of the following Table 8.

TABLE 8

|  | Cosmetic A |
|---|---|
| Ion exchanged water | Balance |
| Ethyl alcohol | 5 |
| Glycerol | 2 |
| Diglycerol | 0.5 |
| Dipropylene glycol | 5 |
| Trehalose | 1.5 |
| Polyethylene glycol 6000 | 1.5 |
| (PEG-240/decyltetradeces-20/HDI) copolymer | 0.5 |
| Sodium acrylate-grafted starch | 0.4 |
| PEG-9 polydimethylsiloxyethyl dimethicone (*1) | 0.05 |
| Dimethicone (*2) | 2 |
| Aminopropyl dimethicone | 0.5 |
| Serine | 0.01 |
| Vitamin E acetate | 0.01 |
| Sodium hexametaphosphate | q.s. |
| Red iron oxide | 0.01 |
| Yellow iron oxide | 0.005 |
| Titanium oxide/mica | 0.2 |
| Synthetic phlogopite/titanium oxide/tin oxide | 0.2 |
| Phenoxyethanol | q.s. |
| EDTA-2Na•2H2O | q.s. |
| Formulated perfume | q.s. |
| Total | 100 |

(*1) and (*2): same as in Table 4

An aqueous thickener solution (B) having the composition of the following Table 9 was separately prepared.

TABLE 9

|  | Aqueous thickener solution (B) |
| --- | --- |
| Ion exchanged water | Balance |
| Glycerol | 22.0 |
| Dipropylene glycol | 18.0 |
| Agar | 1.5 |
| Succinoglycan | 0.4 |
| Phenoxyethanol | q.s. |
| Sodium pyrosulfite | q.s. |
| Total | 100 |

Subsequently, a cosmetic C prepared by mixing the cosmetic A and the aqueous thickener solution B at a mass ratio of 4:1 and the cosmetic A were evaluated in the same manner as described above. Furthermore, whether the pigment powder was precipitated or not was visually observed after being allowed to stand at 50° C. for 4 weeks, and the results were evaluated based on the following criteria.

A: Stable without precipitation of powder
C: Precipitation found

TABLE 10

| Results of evaluation | Cosmetic C (cosmetic A:aqueous thickener solution B = 4:1) | Cosmetic A |
| --- | --- | --- |
| Sherbet-like appearance | A$^+$ | A$^+$ |
| Water collapsing feeling | A$^+$ | A$^+$ |
| No stickiness after application | A | A$^+$ |
| Moisturizing feel | A$^+$ | A |
| Precipitation of powder | A | C |

As it is clear from the results shown in Table 10, the cosmetic A and the cosmetic C of the present invention have a sherbet-like appearance and a water collapsing feeling, and no stickiness was felt after application. Although the cosmetic A gives enough moisturizing feel, the cosmetic C containing an aqueous thickener solution has an increased moisturizing feel. Furthermore, although a pigment powder was precipitated when the cosmetic A containing the pigment powder was allowed to stand for a long time, the precipitation of powder was effectively suppressed by containing of the aqueous thickener solution.

Another formulation example of the cosmetic of the present invention will be given below.

Formulation Example: Gel for Base Make-Up

| Components | Amount (% by mass) |
| --- | --- |
| Ethyl alcohol | 5 |
| Glycerol | 4 |
| Diglycerol | 0.5 |
| Dipropylene glycol | 5 |
| Polyethylene glycol 1500 | 2 |

-continued

| Components | Amount (% by mass) |
| --- | --- |
| Sorbitol | 3 |
| Maltitol | 3 |
| PEG/PPG-14/7 dimethyl ether | 2 |
| PEG/PPG-17/4 dimethyl ether | 0.1 |
| (PEG-240/decyltetradeces-20/HDI) copolymer | 0.5 |
| Sodium acrylate-grafted starch | 0.35 |
| Xanthan gum | 0.01 |
| PEG/PPG-19/19 dimethicone | 0.6 |
| Hydrogenated polyisobutene | 0.6 |
| (Acrylates/alkyl acrylate (C10-30)) crosspolymer | 0.05 |
| Dimethicone | 5 |
| Phenoxyethanol | q.s. |
| Titanium oxide | 0.9 |
| Hyaluronic acid | 0.0001 |
| Chamomile extract | 0.01 |
| Menthol | 0.05 |
| Potassium hydroxide | 0.03 |
| EDTA-2Na•2H$_2$O | q.s. |
| Coloring material | q.s. |
| Perfume | q.s. |
| Ion exchanged water | Balance |

The invention claimed is:

1. A cosmetic base, comprising:
(A) 0.2 to 0.55% by mass, relative to the mass of the cosmetic base, of sodium acrylate-grafted starch; and
(B) 0.3 to 1.0% by mass, relative to the mass of the cosmetic base, of associative thickener having a polyoxyalkylene chain;
wherein
the cosmetic base has a viscosity of 150,000 mPa·s or less.

2. The cosmetic base, according to claim 1, wherein:
said associative thickener (B), having the polyoxyalkylene chain, is at least one thickener selected from the group consisting of (B-1) a hydrophobically modified polyether urethane, (B-2) a hydrophobically modified alkylcellulose and (B-3) a polyacrylate crosspolymer.

3. The cosmetic base, according to claim 2, wherein:
said hydrophobically modified polyether urethane (B-1) has the following formula (I):

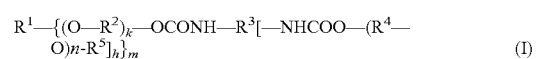

wherein each of $R^1$, $R^2$ and $R^4$ is independently a group selected from the group consisting of an alkylene group having 2 to 4 carbon atoms and a phenyl ethylene group; $R^3$ is a group selected from the group consisting of an alkylene group having 1 to 10 carbon atoms and an alkylene group having 1 to 10 carbon atoms and a urethane bond; $R^5$ is a group selected from the group consisting of a linear alkyl group, branched alkyl group and a secondary alkyl group, which has 8 to 36 carbon atoms; m is a number not smaller than 2; h is a number not smaller than 1; k is a number from 1 to 500; and n is a number from 1 to 200.

4. The cosmetic base, according to claim 3, wherein:
said hydrophobically modified polyether urethane is (PEG-240/decyltetradeces-20/HDI) copolymer.

5. The cosmetic base, according to claim 2, wherein:
said hydrophobically modified alkylcellulose (B-2) is at least one cellulose selected from a group consisting of celluloses having a following formula (II):

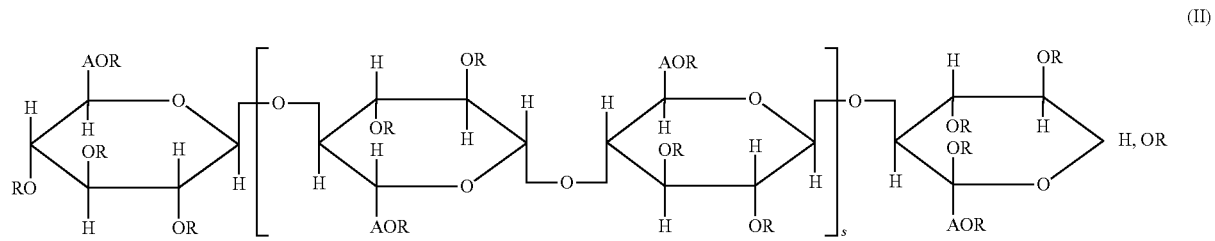

(II)

wherein R is a bonded group $R_1$-$R_2$, wherein $R_1$ is the same or different in one molecule, and is at least one group selected from the group consisting of —[$CH_2CH(CH_3)O$]$_r$—, —[$CH_2CH_2O$]$_r$— and —[$CH_2CH(OH)CH_2O$]$_r$—, wherein r is an integer of 0 to 4, R is at least one group selected from a group consisting of a hydrocarbon group having 12 to 28 carbon atoms, a hydrogen atom and an alkyl group having 1 to 4 carbon atoms, and wherein at least one $R_2$ is a hydrocarbon group having 12 to 28 carbon atoms, A is —$(CH_2)_t$—, wherein t is an integer of 1 to 3, and s is a number from 100 to 10,000.

6. The cosmetic base, according to claim 5, wherein:
said hydrophobically modified alkylcellulose (B-2) is stearoxy hydroxypropyl methylcellulose.

7. The cosmetic base, according to claim 2, wherein:
said polyacrylate crosspolymer (B-3) is polyacrylate crosspolymer-6.

8. A skin cosmetic, comprising:
said cosmetic base according to claim 1.

9. The skin cosmetic, according to claim 8, further comprising:
20% by mass or less of an oil component.

10. The skin cosmetic, according to claim 8, further comprising:
a powder; and
an aqueous thickener other than said component (A) and said component (B).

11. The cosmetic base, according to claim 1, wherein:
the amount of the sodium acrylate-grafted starch (A) is 0.35 to 0.55% by mass, relative to the mass of the cosmetic base, and
the amount of the associative thickener having a polyoxyalkylene chain (B) is 0.3 to 0.8% by mass, relative to the mass of the cosmetic base.

* * * * *